(12) United States Patent
Shaw et al.

(10) Patent No.: US 7,931,563 B2
(45) Date of Patent: Apr. 26, 2011

(54) VIRTUAL TRAINER SYSTEM AND METHOD

(75) Inventors: Rocky Shaw, Redwood City, CA (US); Stephen J. Brown, Woodside, CA (US)

(73) Assignee: Health Hero Network, Inc., Palo Alto, CA (US)

( * ) Notice: Subject to any disclaimer, the term of this patent is extended or adjusted under 35 U.S.C. 154(b) by 49 days.

(21) Appl. No.: 11/683,484

(22) Filed: Mar. 8, 2007

(65) Prior Publication Data
US 2008/0220941 A1 Sep. 11, 2008

(51) Int. Cl.
A63B 71/00 (2006.01)
A63B 69/00 (2006.01)
G09B 9/00 (2006.01)

(52) U.S. Cl. .................. 482/9; 482/8; 434/247

(58) Field of Classification Search .................. 482/1–9; 434/29, 258, 247–255; 700/91; 705/2–4; 709/217
See application file for complete search history.

(56) References Cited

U.S. PATENT DOCUMENTS

| | | | |
|---|---|---|---|
| 5,410,472 A * | 4/1995 | Anderson | 482/9 |
| 5,598,849 A | 2/1997 | Browne | |
| 5,706,822 A * | 1/1998 | Khavari | 600/483 |
| 5,890,997 A * | 4/1999 | Roth | 482/8 |
| 6,066,075 A | 5/2000 | Poulton | |
| 6,527,674 B1 * | 3/2003 | Clem | 482/8 |
| 6,554,776 B1 * | 4/2003 | Snow et al. | 600/532 |
| 6,626,800 B1 * | 9/2003 | Casler | 482/8 |
| 6,682,351 B1 * | 1/2004 | Abraham-Fuchs et al. | 434/247 |
| 6,902,513 B1 | 6/2005 | McClure | |
| 7,166,062 B1 * | 1/2007 | Watterson et al. | 482/8 |
| 7,169,085 B1 * | 1/2007 | Killin et al. | 482/8 |
| 7,212,659 B2 * | 5/2007 | Noro et al | 382/128 |
| 2002/0022551 A1 * | 2/2002 | Watterson et al. | 482/8 |
| 2002/0082144 A1 * | 6/2002 | Pfeffer | 482/8 |
| 2004/0229729 A1 * | 11/2004 | Albert et al. | 482/8 |
| 2005/0079905 A1 | 4/2005 | Martens | |
| 2005/0124463 A1 * | 6/2005 | Yeo et al. | 482/8 |
| 2005/0164832 A1 * | 7/2005 | Maschke | 482/8 |

(Continued)

FOREIGN PATENT DOCUMENTS
EP 1 616 600 A1 1/2008
(Continued)

*Primary Examiner* — Loan Thanh
*Assistant Examiner* — Sundhara M Ganesan
(74) *Attorney, Agent, or Firm* — Rahman LLC

(57) ABSTRACT

A system, apparatus and method for managing health of different individuals by means of a virtual trainer over a network. Reference training data is made available to at least one individual. The exercise motion of the individual or end-user is recorded by using a plurality of sensing elements. The exercise motion of the end-user is processed into a user data. The user data is forwarded to a remote server via a user communication device. A virtual coach application is provided in the remote server that compares the reference training data with the user data and provides a corrective feedback to the end-user. The corrective feedback to the end-user may be provided on the user communication device such as a personal computer, digital assistant, or mobile phone.

28 Claims, 7 Drawing Sheets

U.S. PATENT DOCUMENTS

| | | | |
|---|---|---|---|
| 2005/0164833 A1* | 7/2005 | Florio | 482/9 |
| 2005/0202934 A1* | 9/2005 | Olrik et al. | 482/8 |
| 2005/0233861 A1* | 10/2005 | Hickman et al. | 482/8 |
| 2005/0288154 A1* | 12/2005 | Lee et al. | 482/3 |
| 2006/0025282 A1* | 2/2006 | Redmann | 482/8 |
| 2006/0040793 A1* | 2/2006 | Martens | 482/8 |
| 2006/0205566 A1* | 9/2006 | Watterson et al. | 482/8 |
| 2007/0033068 A1* | 2/2007 | Rao et al. | 705/2 |
| 2007/0033069 A1* | 2/2007 | Rao et al. | 705/2 |

FOREIGN PATENT DOCUMENTS

| | | |
|---|---|---|
| WO | WO 94/02904 | 2/1994 |
| WO | WO 2004/109623 A1 | 12/2004 |
| WO | WO 2005/032363 A1 | 4/2005 |

* cited by examiner

VIRTUAL TRAINER SYSTEM AND METHOD

BACKGROUND

1. Technical Field

The embodiments herein generally relate to health management of individuals and, more particularly to, a health management system that provides an interface between a plurality of expert trainers and a market place of individuals.

2. Description of Related Art

The importance of health management in today's society is well understood. One of the important ways of achieving good health is physical exercise. A number of studies in recent years have revealed the benefits of regular physical exercise. However, if the physical exercise regimen is not correctly followed, then the beneficial effects of physical exercise may be negated.

Therefore, expert trainers are preferred to guide an individual for performing various health exercises and to teach about the correct forms and techniques of physical exercises. The presence of a trainer helps an individual to perform the correct exercising activities and improve the performance of a physical act. The trainer detects and corrects the faults occurring in the physical exercise performance of the individual and instructs the correct manner of performing the exercise. The trainee is therefore considerably dependent upon the skill and experience of the trainer or coach. Moreover, when any exercise movement is fast and complex it may be difficult for the coach to accurately analyze the exercise movement.

Presently, several types of exercising equipment are available that are capable of monitoring and measuring various exercising movements of a person. Further, some types of equipment are capable of monitoring various parameters of the human body such as temperature, pulse, heart rate, blood pressure, movement and the like in order to help the trainer guide the trainee more efficiently. However, this equipment are typically available in a gymnasium and the physical presence of a trainer is still required. Further, in order to obtain the benefits of monitoring of the exercise, the trainee generally has to visit the gymnasium at frequent intervals. This can be inconvenient, particularly when the gymnasium is not located near the user. Further, one gym instructor may attend to the needs of many gym users and hence, each user may not really have the benefit of personal coaching.

Some of the conventional solutions for the above-mentioned problems involve providing various training programs at the user end, so that the user may learn the exercising techniques from these programs. However, success of a training program depends, in part, on the user's technique. The user might not practice the correct motions, and the timings of his/her motion might not be correct. Also, the number of repetitions of a motion might also not be optimal.

Also known in the art are systems and methods for autonomous training, interactive exercise monitoring systems wherein a trainee is trained via a scripted form of training exercise. Input parameters are gathered during a training exercise being performed by the trainee through various types of sensing devices such as sensors placed in running shoes to measure the distance and number of calories burned, heart rate sensors in treadmills and stair steppers, and armband sensors to measure the number of steps taken. However, a feedback on the correct exercise form and a technique of performing exercise is generally not provided by these systems. Further, these systems typically do not set goals for the user to achieve and do not provide any information on how to set a goal and achieve it. These systems also tend to lack in providing a provision to guide the user on the optimal time to switch on to the next exercise, or on how much appropriate weight is to be lifted during a particular exercise in real time. Hence, the user may find difficulty in maintaining proper form and technique. Accordingly, there is a need for a new and improved system, which eliminates the drawbacks of conventional solutions.

SUMMARY

The embodiments herein provide a system, apparatus, and method for managing the health of different individuals by means of a virtual trainer. In one embodiment, a remote server having stored in it a reference training data and a virtual coach application is provided. A plurality of sensing elements for sensing exercise motion of an end-user is also provided. The exercise motion of the end-user is processed to create user data. The user data is forwarded to the remote server via a user communication device. The virtual coach application then compares the reference training data with the user data and provides corrective feedback to the end-user. The corrective feedback to the end-user may be provided on the user communication device such as a personal computer, digital assistant, or mobile phone.

The reference-training data may be based on standard training programs including strength training programs, rehabilitation/physical therapy programs, sports conditioning programs, lose weight programs, gain weight programs, and health-maintenance programs that are recorded in the remote server by an expert trainer. The reference training data may further include the common technique mistakes of the end-user. This data is available to the end-user in multimedia form or text form. An end-user's health management report may also be created that can be accessed by the expert trainer.

The sensing element may be any of a wearable sensing element worn by the end-user, an equipment-sensing element provided on exercising equipment, and a built-in sensing element that is built into the exercising equipment. The exercise motion of the end-user may be based on various parameters including mileage, calories burned, pulse-count, temperature, moisture, tension, time, movement, blood pressure, and repetitions of a movement. The user communication device may be configured to receive the user data by using Bluetooth and/or radio frequency identification (RFID) technology.

Another embodiment provides a method for providing a virtual training system. The method comprises providing reference training data in a remote server; sensing exercise motion of an end-user by using a plurality of sensing elements; creating user data based on the exercise motion of the end-user; transmitting the user data via a user communication device to the remote server; comparing the reference training data with the user data by providing a virtual coach application present in the remote server; and providing a corrective feedback to the end-user.

Another embodiment provides a sensor data management apparatus. The apparatus comprises an accelerometer for detecting the exercise motion of an end-user; a microprocessor configured to create user data based on the exercise motion of the end-user; a transmitter configured to transmit the user data to a user communication device. The apparatus further comprises a rechargeable power storage device; a power source; a real-time clock; and memory devices for storing data being processed by the microprocessor.

These and other aspects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF THE DRAWINGS

The embodiments herein will be better understood from the following detailed description with reference to the drawings, in which.

DETAILED DESCRIPTION OF THE PREFERRED EMBODIMENTS

Figure 1:
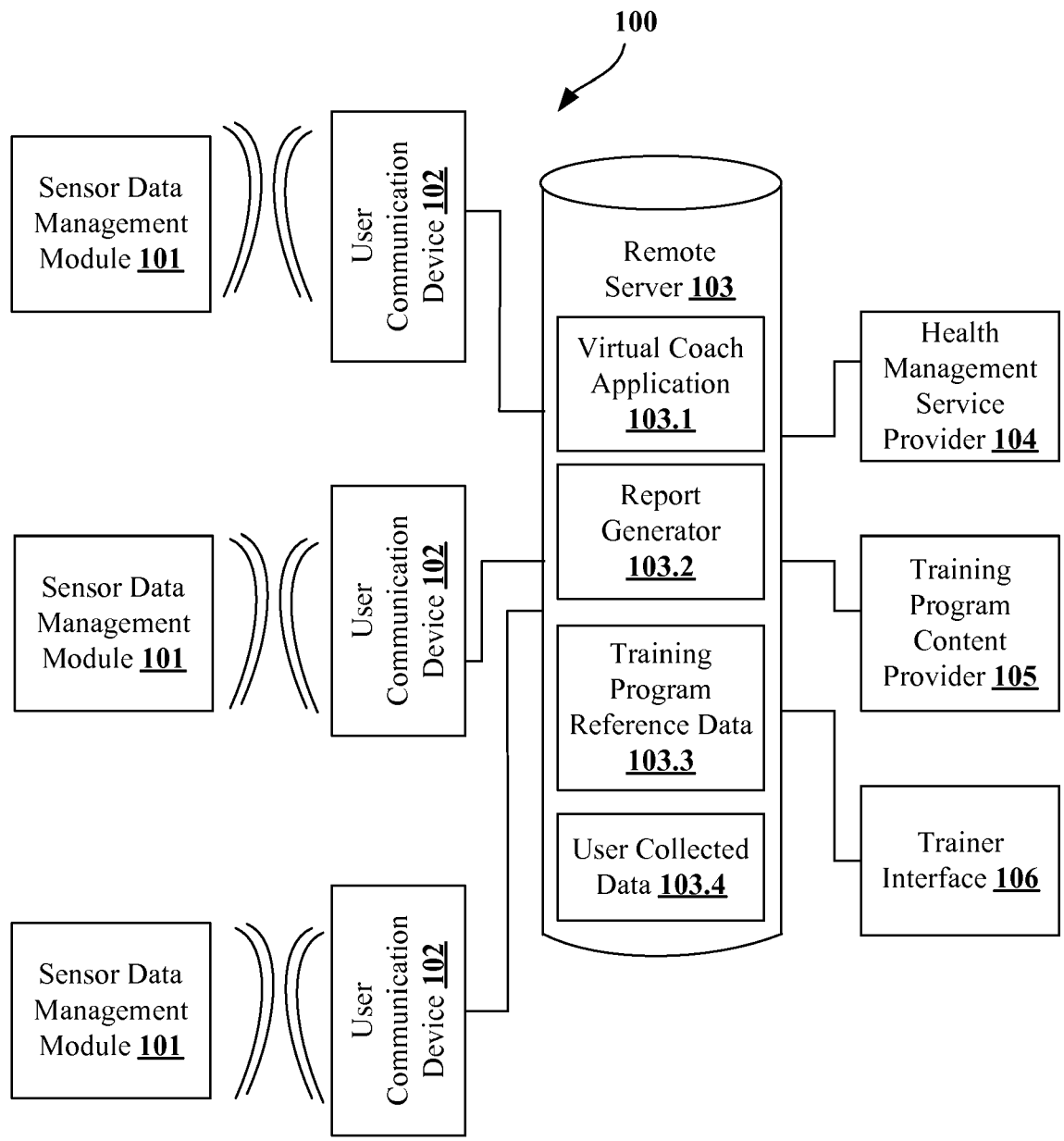
FIG. 1 is a block diagram illustrating a virtual training system according to an embodiment herein.

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

As mentioned, there remains a need for a new and improved health management system. The embodiments herein achieve this by providing a system, apparatus, and method for managing health of different individuals by means of a virtual trainer over a network. In one embodiment, reference training data is made available to at least one individual. The exercise motion of the individual or end-user is recorded by using a plurality of sensing elements. The exercise motion of the end-user is processed into user data. The user data is forwarded to a remote server via a user communication device. A virtual coach application is provided in the remote server that compares the reference training data with the user data and provides a corrective feedback to the end-user. The corrective feedback to the end-user may be provided on the user communication device such as a personal computer, digital assistant, or mobile phone. Referring now to the drawings, and more particularly to FIGS. 1 through 7, where similar reference characters denote corresponding features consistently throughout the figures, there are shown preferred embodiments.

FIG. 1 shows a block diagram illustrating a virtual training system (VTS) 100 according to an embodiment herein. The system 100 comprises a plurality of sensor management data modules 101 that are adapted to receive different (health-related) data, such as exercise motion of an end-user 702 (of FIG. 7), from various sensing elements 400 (shown in FIG. 4). The sensor data management module or apparatus 101 preferably comprises electronic equipment having a microprocessor (not shown) to process the data received from the various sensing elements 400 (shown in FIG. 4). The microprocessor of the sensor data management data modules 101 creates user data by processing the data related to the exercise motion of the end-user.

One or more user communication devices 102 may be communicatively coupled to the sensor data management module 101 for receiving the user data created by the microprocessor and transmitting the same to a remote server 103 over a network. The remote server 103 is preferably a World Wide Web server and the network is preferably the Internet. It will be apparent to one skilled in the art that the server 103 may comprise a single stand-alone computer or multiple computers distributed throughout a network. The user communication device 102 is preferably a personal computer, remote terminal, a personal digital assistant, a mobile telephone, or web television (TV) unit connected to the server 103 via the Internet. The user communication device 102 functions as a remote interface for entering in the server 103 messages and health-related data to be communicated to the end-users.

The sensor data management module or apparatus 101 is designed to interact with a user in accordance with script programs received from the remote server 103 over the network. Each apparatus 101 is in communication with the server 103 through the communication network. Alternatively, each apparatus 101 may be placed in communication with the server 103 via wireless communication networks, cellular networks, telephone networks, satellite networks, or any other network which allows each apparatus 101 to exchange data with the server 103. It is to be understood that the system 100 may include any number of sensor data management module or apparatuses 101 for monitoring any number of individuals.

The remote server 103 may provide a web-based application, which can be accessible to an end-user through his/her user communication device 102. The end-user generally accesses the virtual coach application 103.1 stored in the remote server 103. The remote server 103 has reference training data 103.3. The reference training data 103.3 may be obtained from health management service providers 104 and training program content providers 105. The reference training data 103.3 may contain digital audio recordings and digital video recordings of exercise-training programs and techniques of expert trainers based on standard or customized training program goals. The reference training data 103.3 may also include common technique mistakes of the end-users in multimedia form or text form. The expert trainer may record, update or modify their program content via trainer interface 106. Generally, the expert trainers may utilize the virtual trainer application program 103.1 to record techniques and proper form when using exercise equipment. An end-user of the virtual trainer system 100 may record their form and technique based on training program goals.

As explained above, the user data is generally the measured and monitored exercise motion of an end-user seeking the training. This data is compared with the reference-training program of the expert trainer and a corrective feedback is provided to the end-user on his/her communication device 102. The remote server 103 further stores the user data of multiple users as user collected data 103.4. A report generator 103.2 is also provided in the remote server 103 for creating health management reports for trainers, physical therapists, and healthcare providers, detailing progress and goal attainment. The report generator 103.2 is designed to generate a health report from the responses and the measurements of exercise equipment received in the server 103. The health report is displayed on the user communication device 102. The health report may include a graph of the measured exercise movements performed on exercise equipment by the end-user, or a listing of the responses received from the end-users with respect to the health-related script. Specific techniques for writing a report generator program to display data in this manner are well known in the art. The virtual coach application 103.1 identifies incorrect form/technique and other assessment data and then prompts the end user to action during exercise in terms of feedback as explained above.

Figure 2:
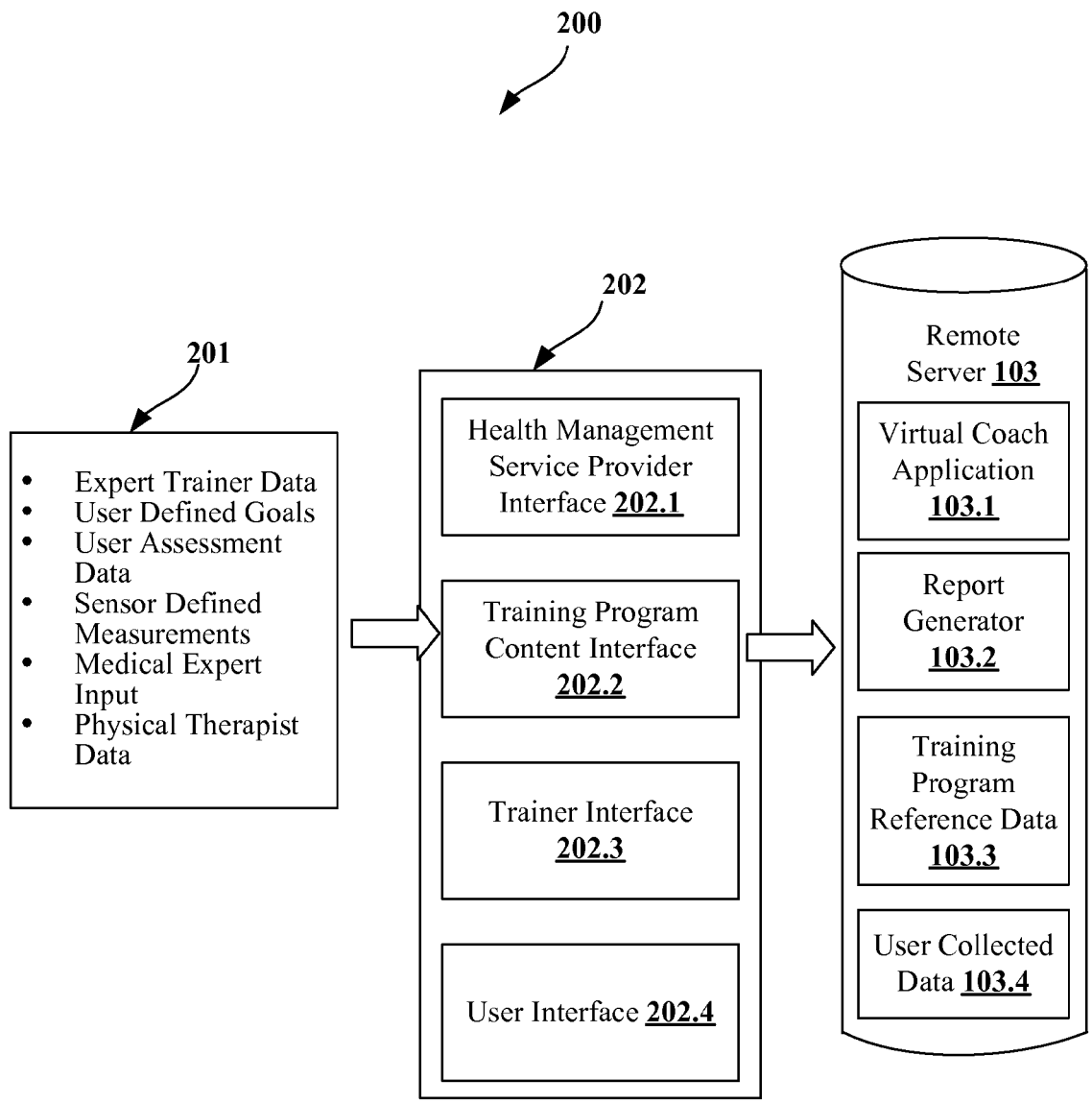
FIG. 2 is a diagram illustrating training content creation according to an embodiment herein.

FIG. 2 shows a diagram of training content creation 200 Training programs may be derived from expert trainer movements/techniques. Expert trainers may record the motion associated with their recommended techniques along with coaching and education for the end-users on how to properly perform the technique. The programs may include a set of key measurements relating to education, behavior, and knowledge associated with an end-user's training program goals. The training content creation flow includes disparate sources of data 201 populating the numerous VTS interfaces 202. The disparate sources of data may include expert trainer data, user defined goals, user assessment data, sensor defined measurements, medical expert input, and physical therapist data. As previously mentioned, disparate sources of data 201 populate numerous VTS interfaces 202 including health management service provider interface 202.1, training program content interface 202.2, trainer interface 202.3, and user interface 202.4. For instance, the health management service provider interface 202.1 may collect inputs from medical experts and physical therapists pertaining to recommended physical exercise techniques for the end-users and information on how to perform the technique. The information may be in the form of audio, video, or written script. Similarly, training program content interface 202.2 may gather information on various kinds of exercise techniques from expert trainers. The trainer interface 202.3 may also gather information on how to perform the correct exercise techniques from expert trainers. The user interface 202.4 may collect various data such as exercise motion of an end-user, from various sensing elements 400 (shown in FIG. 4). These interfaces 202 then transfer the populated data to the remote server 103 for analysis and storage. Thereafter, the feedback is prompted on the end-user's communication device 102 (of FIG. 1) after the content has been compared to the individual's goals using the virtual coach application 103.1 (of FIG. 1).

Within the context of the embodiments herein, examples of training program goals include strength training, rehabilitation/physical therapy, sports conditioning (professional athletes/Olympians/college athletes), weight management (weight gain or loss), health maintenance, etc.

Figure 3:
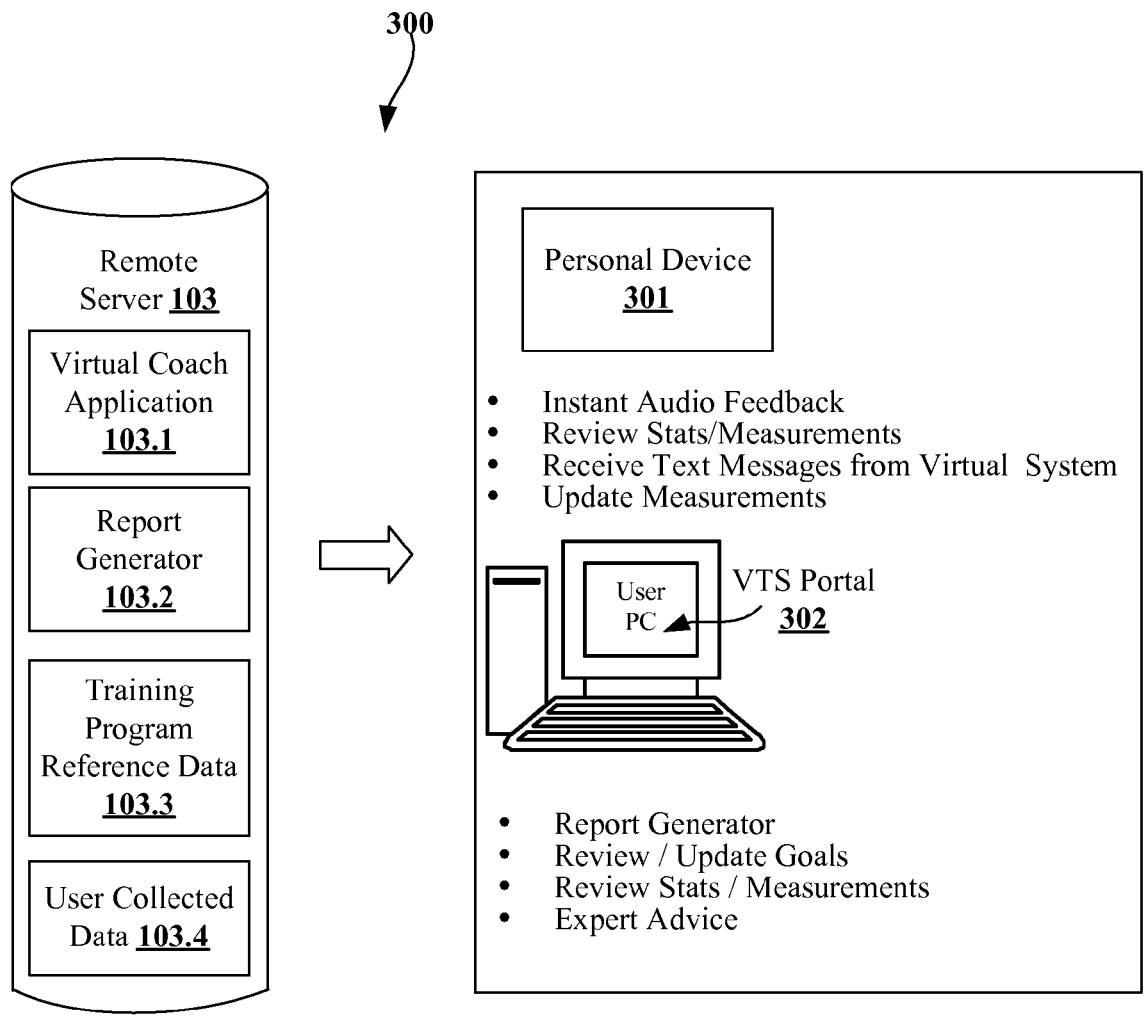
FIG. 3 is a flow diagram illustrating training process feedback according to an embodiment herein.

FIG. 3 illustrates a diagram for training process feedback 300. Data populated in the remote server 103 (of FIG. 1) from the interfaces 202 (of FIG. 2) are assessed and analyzed based on end-user goals and delivered through a personal device 301 and VTS portal 302. The personal device 301 may receive the corrective feedback in terms of an instant audio feedback, stats/measurements review, and text messages from the virtual system 100 (of FIG. 1) and updated measurements as shown in FIG. 3. For instance, if an end-user performs any exercise motion incorrectly or commits some common technique mistake, then a corrective feedback from the virtual training system 100 (of FIG. 1) may be sent which might be indicated as an instant audio feedback such as an alarm or a buzz of the personal device 301. On the personal device 301, the end-user may also receive reviews and text messages pertaining to the measurements recorded at user's end so that he/she may correct his/her performance accordingly. The end-user may also receive updated measurements from the virtual training system 100 (of FIG. 1).

Similarly, the VTS portal 302 may display the corrective feedback through several hyperlinks including report generator, review/update goals, review stats/measurements, and expert advice. A report generator at the VTS portal 302 may display health management reports for end-user review. The report may be generated based on the measurements of exercises performed by the end-user. The health report may include, for example, a graph of the measured exercise movements performed on exercise equipment by the end-user. Since an end-user follows the reference training data 103.3 that is based on the information provided by health management service providers 104 (of FIG. 1) and training program content providers 105 (of FIG. 1), hence, any update in the reference training data will be reflected at the VTS portal 302 for end-user's review. The review/update goals at the VTS portal 302 displays the programs and goals that are updated or modified by the expert trainers via trainer interface 106 (of FIG. 1).

Similarly, the review stats/measurements may provide the statistics and the measurements of the exercises performed by the end-user. The VTS portal 302 may also display expert advice depending upon the requirements of an end-user. For example, if an end-user is diabetic, then he might require expert advice pertaining to sugar free diet, medications, or information on exercises specifically designed for diabetic patients.

Figure 4:
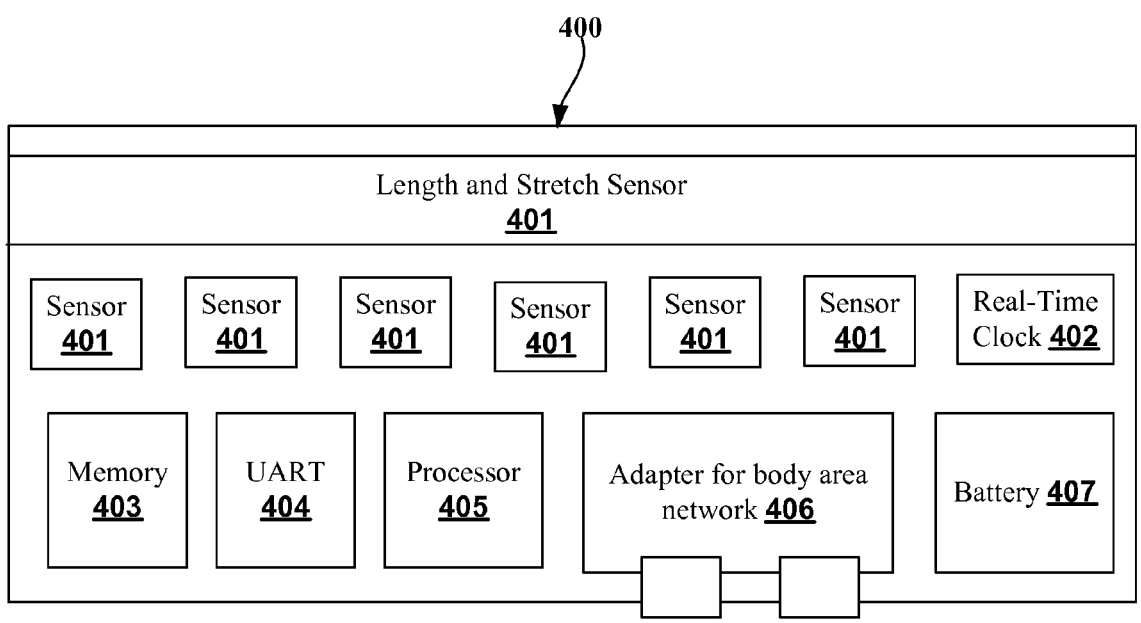
FIG. 4 shows a wearable sensing element according to an embodiment herein.

FIG. 4 shows a sensing element 400 capable of being worn by an end-user. The wearable sensing element 400 may be provided in the form of a sensor band that can be worn on the arm, chest, or leg or other body part of an end-user for sensing various exercise motion of the user, wherein the sensing element 400 comprises a plurality of sensors 401. These various exercise motions may be further processed by a processor 405 as shown. A memory component 403 is also provided to store the data being processed by the processor 405. Power supply may be provided with the help of a battery 407 or any other equivalent supply source. The wearable sensing element 400 is also provided with a real time clock 402 for the operation of the processor 405. A transmitter (for example, a universal asynchronous receiver/transmitter (UART)) 404 is provided in the wearable sensing element 400 to transmit the processed data to the sensor management data apparatus 101 (of FIG. 1) as described above. Furthermore, an adapter for body area network 406 is provided for receiving data from sensors present on the human body and transmitting the data to the remote server 103 (of FIG. 1) via the user communication device 102 (of FIG. 1).

Figure 5:
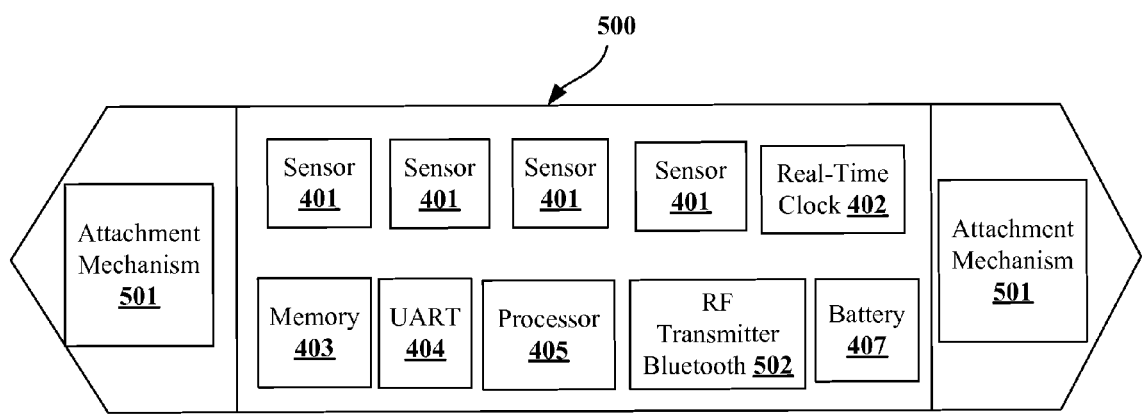
FIG. 5 shows an equipment-sensing element according to another embodiment herein.

FIG. 5 shows the sensing element 400 (of FIG. 4) in the form of an equipment sensor 500 that may be provided on the exercising equipment (not shown) to sense the different movements, vibration, and motion of the equipment that are being used by the user. In one embodiment, the equipment sensor 500 may be secured to the user/equipment using an attachment mechanism 501. Similar to the wearable sensing element 400 (of FIG. 4) the equipment sensor 500 senses the exercise motion of the user using that equipment and this motion is converted into digital form by the processor 405. The digital data is then transferred to the remote server 103 via the user communication device 102 (of FIG. 1).

The wearable sensing elements 400 and equipment sensing elements 500 function in a similar manner. The wearable sensing elements 400 send the measured data to the sensor data management module or apparatus 101 (of FIG. 1) via body area network 406. On the other hand the equipment sensing elements 500 send the measured data to the sensor data management module or apparatus 101 (of FIG. 1) via RF transmitter & Bluetooth™ transmission 502.

In one embodiment, the equipment sensor 400 (of FIG. 4) may be provided in the form of built-in sensors that can be built inside exercising equipment. The built-in sensors comprise various sensors 401 and an accelerometer to sense and detect the motion of an exercise machine that is being used by the user. This allows the form and technique followed by the user to be recorded and sent in digital form to the remote server 103 (of FIG. 1) by the UART transmitter 404 (of FIG. 4).

Figure 6:
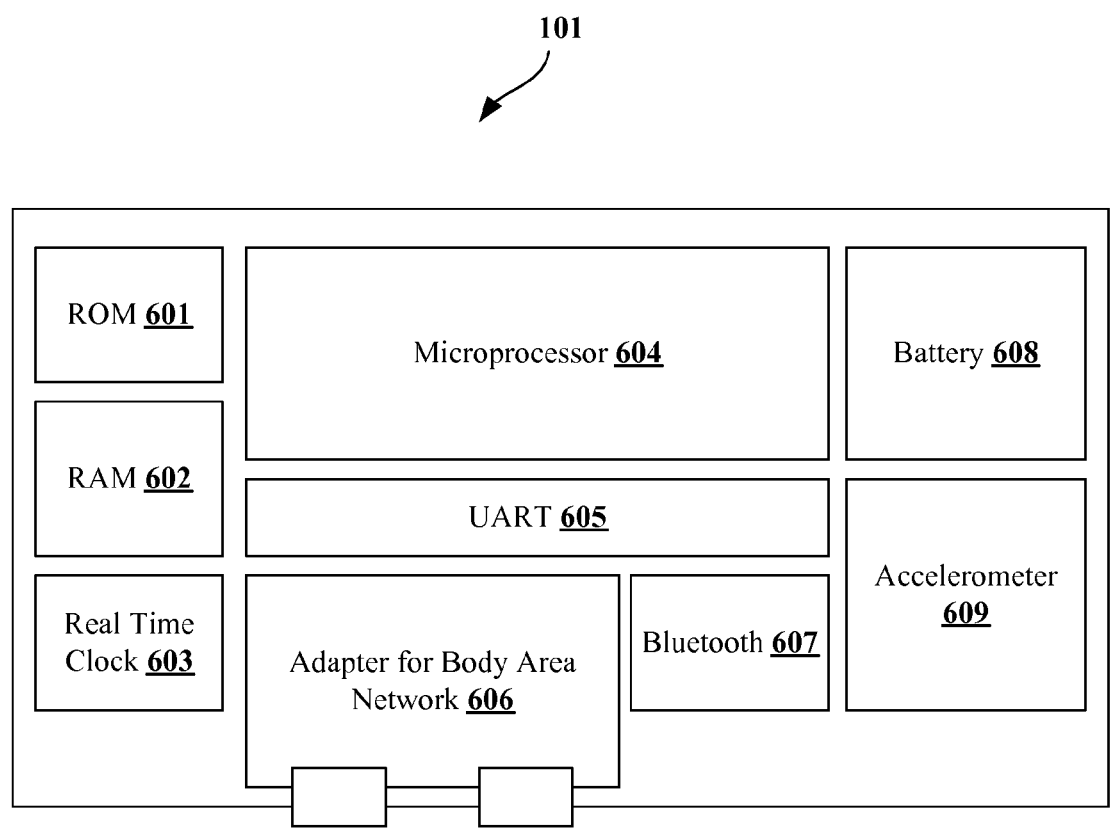
FIG. 6 shows a built-in sensing element according to another embodiment herein.

FIG. 6 shows a detailed view of the sensor data management apparatus 101 (of FIG. 1) according to an embodiment herein. The apparatus 101 (of FIG. 1) comprises an accelerometer 609 for detecting the exercise motion of an end-user; a microprocessor 604 adapted to create user data based on the exercise motion of the end-user; memory devices such as read-only memory (ROM) 601 and random access memory (RAM) 602 are connected to the microprocessor 604. The random access memory RAM 602 is provided to store various data and information that are to be used by the microprocessor 604. The ROM 601 stores firmware for controlling the operation of the apparatus 101. The firmware includes a script interpreter used by the microprocessor 604 to execute the script programs.

The microprocessor 604 is also connected to a real-time clock 603. The real-time clock 603 indicates the current date and time to the microprocessor 604. For clarity of illustration, clock 603 is shown as a separate component, but is preferably built into the microprocessor 604. The microprocessor 604 processes the data received from the various sensing elements 400 (of FIG. 4) and the remote server 103 (of FIG. 1). A transmitter 605 adapted to transmit the user data to the user communication device 102 (of FIG. 1) is also provided in the apparatus 101. The apparatus 101 further comprises a rechargeable power storage device (for example, a battery) 608. The apparatus 101 is further adapted to transmit the user data to the user communication device 102 (of FIG. 1) by using Bluetooth™ technology 607 or RFID technology or both. The user communication device 102 (of FIG. 1) operates under the control of the microprocessor 604 to collect measurements from the end-users performing the exercises and to output the measurements to the microprocessor 604 for storage in the memory. An adapter for body area network 606 is also provided for receiving data from sensors present on the human body and transmitting the data to the remote server 103 (of FIG. 1) via the user communication device 102 (of FIG. 1).

Figure 7:
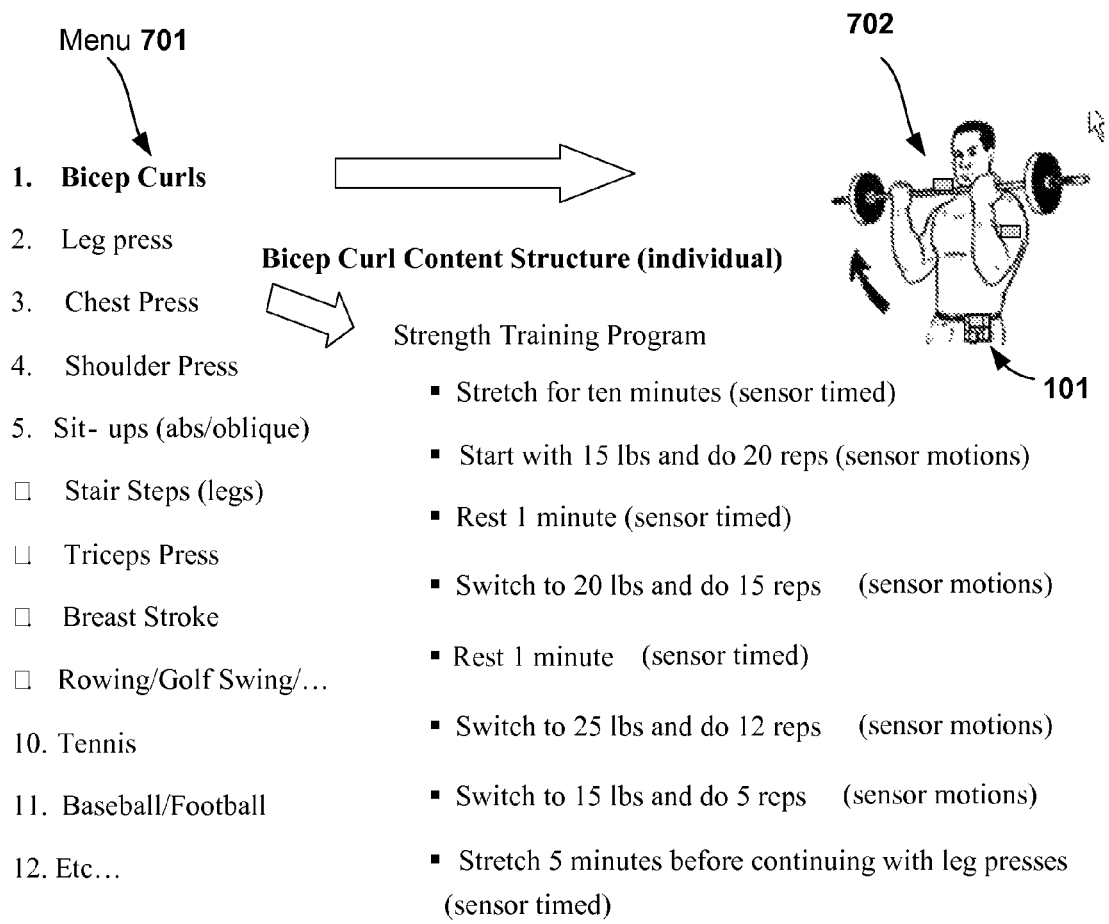
FIG. 7 shows a sample training program according to an embodiment herein.

FIG. 7 shows a sample training program as embodied as a computer-executable set of instructions. The end-user 702 is shown wearing the sensor data management apparatus 101 and performing the exercises according to a specified training program. FIG. 7 shows, as an example, a method of performing bicep curls as selected from a menu 701 of various types of exercises/activities. When an end-user 702 is performing 'bicep curls' on his exercise equipment, he/she may refer to the detailed content structure from the menu 701 and follow the correct form and technique. The end-user 702 may refer to the detailed content structure on his communication device 102 (of FIG. 1). Similarly, the end-user 702 can perform various exercises by referring to other program content structures from the menu 701 such as leg press, chest press, etc., provided by various health providers and trainers.

The above-described training program content may also include a set of queries, and for each of the queries, corresponding response choices. Such queries may be sent to the end-user on his/her communication device 102 (of FIG. 1) that functions as a remote interface for the end-users. The user may input his/her response by using input buttons of the communication device 102 (of FIG. 1). The training program content further includes a prescribed connection time for each apparatus 101 to establish a subsequent communication link to the remote server 103 (of FIGS. 1 and 2). The content structure is generally entered in the server 103 by a healthcare provider, such as the end-user's physician, trainer or case manager. Furthermore, any person desiring to communicate with the user may also be granted access to the server 103 to create and assign training programs. Moreover, the system 100 may include any number of remote interfaces 202 (of FIG. 2) for entering training program generation and program assignment information in the server 103.

Again, with respect to FIGS. 1 and 2, a training program may be generated from the information entered in the interface 202. The script program is stored in the remote server database 103. Multiple training programs may be generated for multiple users. Each user to be monitored is preferably provided with his or her own remotely programmable apparatus 101, which has a user's unique identification code stored therein. Each user is thus uniquely associated with a respective one of the apparatuses 101. If an apparatus 101 is connected, the server 103 receives from the apparatus 101 the user's unique identification code. The server 103 receives from the apparatus 101 the query responses, device measurements, and training identification code recorded during execution of a previously assigned training program. The training identification code identifies to the server 103 which script program was executed by the apparatus 101 to record the query responses and device measurements. The responses, device measurements, and script identification code are then stored in a database of the server 103.

Generally, the embodiments herein provide a network-based system 100 that serves as the interface between a plurality of expert trainers and a plurality of end-users 702. A user can subscribe to a program of a particular trainer and have real-time coaching, education, and feedback on proper exercise technique without the trainer being physically present with the user because, when a user practices the technique, the virtual coach compares the user's range of motion recording to the expert recording, and branches to appropriate feedback, thus providing a virtual coaching system 100 for proper exercise technique on each exercise as part of an overall fitness program authored by an expert trainer.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the appended claims.

What is claimed is:

1. A virtual trainer system comprising:
    a remote server that is remotely located from a user, stores a computer-executable report generator that creates user health management reports and is accessed by said user and entities other than said user, wherein said entities comprise other users and said report generator is executed by said remote server;
    reference training data stored in said remote server, wherein said reference training data is common for said user and said entities;
    at least one sensing element that senses exercise motion of said user;
    a processor that creates user data based on the sensed exercise motion of said user;
    a user communication device that receives said user data and transmits said user data to said remote server, wherein said user communication device is remotely located from said remote server; and
    a virtual coach application component stored in said remote server and comprising computer-executable instructions executed by said remote server, wherein said computer-executable instructions compare said reference training data with said user data and provides corrective feedback to said user.

2. The virtual trainer system of claim 1, wherein said reference training data comprises training programs created, updated, and modified by an expert trainer.

3. The virtual trainer system of claim 2, wherein said remote server comprises a web server and said user health management reports are accessible by said user and said expert trainer via a web interface.

4. The virtual trainer system of claim 1, wherein said reference training data is accessible to said user in any of multimedia form and text form.

5. The virtual trainer system of claim 2, wherein said training programs include a strength training program, a rehabilitation/physical therapy program, a sports conditioning program, a weight management program, and a health-maintenance program.

6. The virtual trainer system of claim 1, wherein the sensing element is attached to said user.

7. A virtual trainer system comprising:
    exercising equipment operated by a user;
    a remote server that is remotely located from a user, stores a computer-executable report generator that creates user health management reports, and is accessed by said user and entities other than said user, wherein said entities comprise other users, said report generator is executed by said remote server;
    reference training data stored in said remote server, wherein said reference training data is common for said user and said entities, and wherein modification of said reference training data is reflected to said user and said entities connected to said remote server;
    at least one sensing element that senses exercise motion of said user, wherein said at least one sensing element comprises an equipment-sensing element that is attached to said exercising equipment;
    a processor that creates user data based on the sensed exercise motion of said user;
    a user communication device that receives said user data and transmits said user data to said remote server, wherein said user communication device is remotely located from said remote server; and
    a virtual coach application component stored in said remote server and comprises computer-executable instructions executed by said remote server, wherein said computer-executable-instructions compare said reference training data with said user data and provides corrective feedback to said user, wherein said user data is accessible to said other users.

8. The virtual trainer system of claim 1, wherein the sensing element is configured in exercising equipment.

9. The virtual trainer system of claim 1, wherein the exercise motion comprises a plurality of exercise parameters of said user.

10. The virtual trainer system of claim 9, wherein said exercise parameters comprise any of mileage, calories burnt, pulse-count, temperature, moisture, tension, time, and blood pressure.

11. The virtual trainer system of claim 1, wherein said reference training data comprises common technique mistakes of said user.

12. The virtual trainer system of claim 1, wherein said corrective feedback is provided on said user communication device.

13. The virtual trainer system of claim 1, wherein said user communication device wirelessly receives said user data.

14. The virtual trainer system of claim 1, wherein said user communication device comprises any of a personal computer, a personal digital assistant, and a mobile telephone.

15. A method for providing virtual coaching, said method comprising:
    storing reference training data in a remote server that is remotely located from a user, said remote server being accessed by said user and entities other than said user, wherein said entities comprise other users;
    sensing exercise motion of said user by using a plurality of sensing elements;
    creating user data in a user communication device based on the sensed exercise motion of said user;
    transmitting said user data from said user communication device to said remote server, wherein said user communication device is remotely located from said remote server;
    comparing said reference training data with said user data using a virtual coach application component stored and executed on said remote server;
    creating a report from the comparisons of said reference training data with said user data using a report generator stored and executed on said remote server, wherein said report is accessible by said user; and
    providing corrective feedback to said user based on the comparisons of said reference training data with said user data.

16. The method of claim 15, wherein said reference training data comprises training programs created by an expert trainer.

17. The method of claim 16, wherein said remote server stores a computer-executable application that creates user health management reports accessible by said expert trainer.

18. The method of claim 15, wherein said reference training data is accessible to said user in any of multimedia form and text form.

19. The method of claim 16, wherein said training programs includes a strength training program, a rehabilitation/physical therapy program, a sports conditioning program, a weight management program, and a health-maintenance program.

20. The method of claim 15, wherein the sensing element is attached to said user.

21. The method of claim 15, wherein the sensing element comprises an equipment-sensing element that is attached to exercising equipment.

22. The method of claim 15, wherein the sensing element is configured in exercising equipment.

23. The method of claim 15, wherein the exercise motion comprises a plurality of exercise parameters of said user.

24. The method of claim 23, wherein said exercise parameters comprise any of mileage, calories burnt, pulse-count, temperature, moisture, tension, time, and blood pressure.

25. The method of claim 15, wherein said reference training data comprises common technique mistakes of said user.

26. The method of claim 15, wherein said corrective feedback is provided on said user communication device.

27. The method of claim 15, wherein said user communication device wirelessly receives said user data.

28. The method of claim 15, wherein said user communication device comprises any of a personal computer, a personal digital assistant, and a mobile telephone.

* * * * *